United States Patent [19]

Flachslaender

[11] Patent Number: 5,692,512
[45] Date of Patent: Dec. 2, 1997

[54] BLOOD PRESSURE MEASURING MODULE

[75] Inventor: Erwin Flachslaender, Calw-Stammheim, Germany

[73] Assignee: Hewlett-Packard Company, Palo Alto, Calif.

[21] Appl. No.: 713,053

[22] Filed: Sep. 12, 1996

[30] Foreign Application Priority Data

Oct. 19, 1995 [EP] European Pat. Off. ............ 95116470

[51] Int. Cl.⁶ .................................................. A61B 05/00
[52] U.S. Cl. ............................ 128/677; 128/672; 128/687
[58] Field of Search ........................... 128/672, 677–687, 128/688–690

[56] References Cited

U.S. PATENT DOCUMENTS

| | | |
|---|---|---|
| 3,954,099 | 5/1976 | Raczkowski et al. . |
| 4,862,895 | 9/1989 | Yamasawa et al. ............... 128/686 |
| 4,898,180 | 2/1990 | Farrelly et al. ................. 128/681 |
| 5,220,925 | 6/1993 | Hishida ........................ 128/686 |
| 5,335,665 | 8/1994 | Suzuki ......................... 128/686 |
| 5,375,605 | 12/1994 | Speidel ........................ 128/677 |

FOREIGN PATENT DOCUMENTS

| | | |
|---|---|---|
| 0180662A1 | 8/1984 | European Pat. Off. . |
| 124308A3 | 12/1984 | European Pat. Off. . |
| 465192A1 | 1/1991 | European Pat. Off. . |

OTHER PUBLICATIONS

European Search Report, EP 95 11 6470, 16 Apr. 1996.

*Primary Examiner*—Robert Nasser

[57] ABSTRACT

Apparatus for measuring blood pressure is housed in a hermetically sealed, small casing, which is sealed in dust, water and pressure-tight manner by a film on the outside of the casing's cover and on the casing's underside. Pneumatic connecting lines are integrated into the casing cover and consequently separate the pressure-side area from the pressureless area in the casing interior. The casing interior contains a pump for filling a blood pressure cuff that is connectable to the apparatus, a valve for the controllable venting of the cuff, pneumatic connecting lines, pressure sensors and an electric control circuit and electric connecting lines. As a result of the construction according to the invention it is possible to obtain a high integration density and therefore a very small and compact blood pressure measuring module.

8 Claims, 4 Drawing Sheets

BLOOD PRESSURE MEASURING MODULE

FIELD OF THE INVENTION

The present invention relates to an apparatus for measuring blood pressure (blood pressure measuring module) for connection to a correspondingly designed display and evaluating unit.

BACKGROUND OF THE INVENTION

For non-invasive blood pressure measurements, use is made either of a manual blood pressure measurement or an automatic blood pressure measurement. In the known manual blood pressure measurement a cuff applied to the arm of the patient is inflated and then on release the blood pressure is measured by listening to the Korotkoff signals. In the automatic measurement on releasing the air the blood pressure is measured by observation of the high frequency fluctuations superimposed on the pressure signal (so-called oscillatory method).

In the automatic method, to which the present invention relates, it is at least necessary to have an air pump, various valves and pressure sensors. These electropneumatic components are normally wired together electrically by means of individual stranded wires in the form of a cable harness. The air-carrying connections are normally in the form of hoses, so that this technology when integrating the components into a casing generally requires much space for the components and the assembly manipulations. In addition, sealing takes place with profile washers, O-rings or joint packings. For this purpose it is necessary to have space-consuming mounting flanges, screw couplings, etc. and welding processes require complicated and expensive machines, the material selection simultaneously being restricted. All this leads to complicated and costly equipment.

The problem of the present invention is therefore to propose an integration and in particular maximum integration of the electropneumatic components permitting a miniaturized and lower cost blood pressure measuring module.

This problem is solved by a blood pressure measuring module having the features of the main claim. Further advantageous developments can be gathered from the subclaims.

SUMMARY OF THE INVENTION

The blood pressure measuring module according to the invention contains a hermetically sealed small casing, which is sealed in dust, water and pressure-tight manner on the outside of a casing cover and on the casing underside by means of a film or sheet. This hermetic seal is intended to ensure that during cleaning no contaminants can enter the interior of the small casing and also no dust or pollutant sucked in through the air can pass out of the interior of the casing. On the casing underside the small casing can also have a base or can be directly closed by means of a corresponding, mechanically stable film. The casing has the electropneumatic components necessary for operation. These are constituted by a pump for filling a blood pressure cuff connectable to the apparatus, a valve for the controllable venting of the cuff, pneumatic connecting lines, a pressure sensor and an electric control circuit and electric connecting lines for the control of the components necessary for the particular function. The pneumatic connecting lines are integrated into the casing cover and the latter is so designed that it separates the pressure-side area from the pressureless, inner casing area. This casing cover design permits a significant reduction in the casing size, because the pneumatic connecting lines can be produced without hoses. Thus, in the interior of the casing cover is located the pressure-side area, separated by the wall facing the components. By means of a mechanically stable support film the outside of the cover is hermetically sealed and therefore the pressure-side area is limited to the interior of the cover. The cover has on its side facing the components openings used for connecting the components to the pneumatic connecting lines located in the cover.

According to a preferred embodiment the casing comprises a casing frame and a casing cover connected thereto and which are made by plastic injection moulding, the casing cover and casing frame preferably being in one piece. Such a construction of the small casing and the use of the plastics material permits a further miniaturization of the blood pressure measuring module. The components can be fixed to the casing frame by means of snap catches, so that they are fixable in inexpensive, simple and reliable manner in the casing. The connection of the casing frame to the cover so as to constitute a one-piece part also contributes to the reduction in size and simplification of the module.

The production of the cover as a plastic injection moulding, according to a preferred development of the invention, permits the housing of the pneumatic connections in the cover in the form of already injected ducts. This allows a further miniaturization and economizes on additional, separated and separately fittable hoses and the like.

According to another preferred embodiment the films located on the top of the casing cover and on the casing underside are in the form of stable support films. This brings about the reliable sealing of the pressure area on the top of the casing cover and on the casing underside, so that no additional casing bottom is required. According to a preferred development the films are provided as mechanically stable support films with a hot-melt adhesive coating which is melted onto the plastics casing part in the heat sealing process. The hot-melt adhesive coating can e.g. be polyurethane based.

Another step in miniaturizing the blood pressure measuring module is achieved in that the electric control circuit comprises a flexible printed circuit board with integrated electrical connecting lines and electronic components. This electronic control circuit is connected to a miniature diaphragm pump, microvalves and pressure sensors. The flexible circuit board is passed out of the casing for connection to a voltage source and a control unit.

The invention consequently provides a solution as to how the corresponding components can be integrated and miniaturized in a blood pressure measuring module. Through the additional sealing by means of the heat sealable film, contaminants neither enter, nor leave the module, e.g. in the form of pump dust. Such a miniaturized blood pressure measuring module consequently provides an inexpensive blood pressure reception unit for further integration into an overall apparatus with evaluating circuit and display. The blood pressure measuring module according to the invention is characterized by its very compact construction, simple assembly and smallness. Also no additional sealing and assembly elements are required.

BRIEF DESCRIPTION OF THE DRAWINGS

The invention is described in greater detail hereinafter relative to a nonlimiting embodiment and the attached drawings, wherein show.

DETAILED DESCRIPTION OF THE INVENTION

Figure 1:
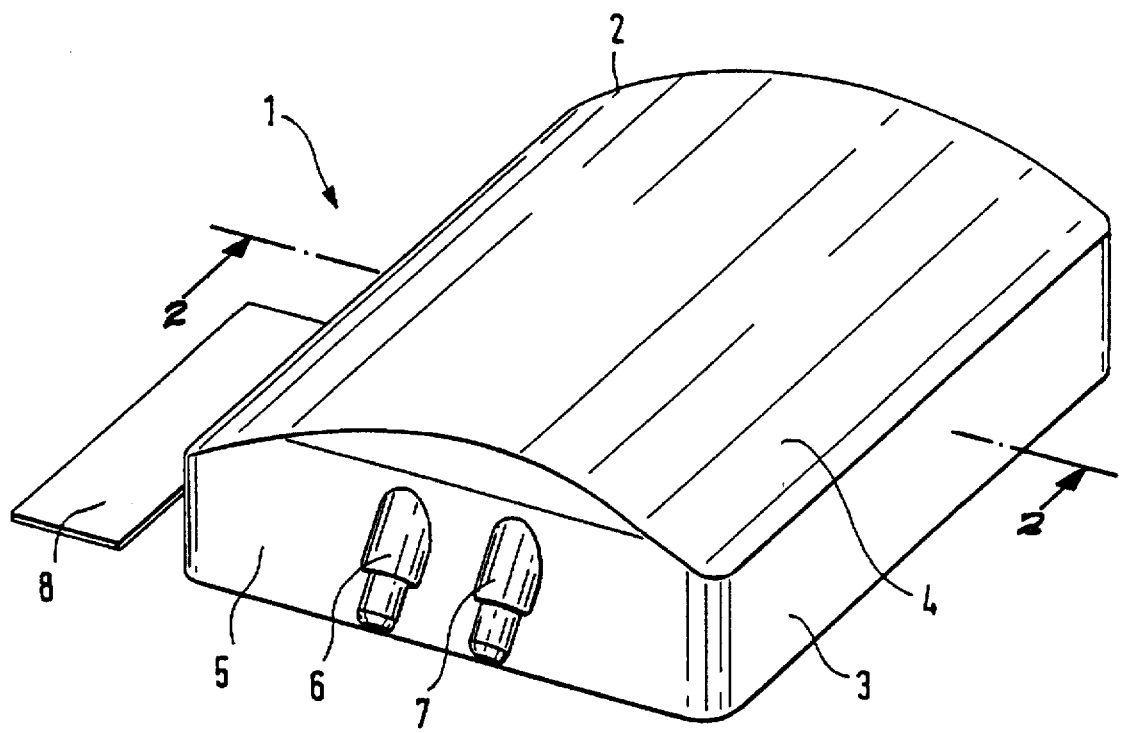
FIG. 1: A perspective view of a complete blood pressure measuring module.

The blood pressure measuring module 1 is shown perspectively in FIG. 1. The casing 2 of the blood pressure measuring module 1 is formed from plastic from the casing frame 3 and the casing cover 4 connected in one piece thereto. On the front side 5 are provided two air passages 6, 7, whereof one is used for the connection of a blood pressure measuring cuff and the other for air suction. FIG. 1 also shows the connecting lug 8, passed out of the module for the electrical connection of said module 1 to a not shown evaluating and display unit into which the blood pressure measuring module 1 can be integrated.

Figure 2:
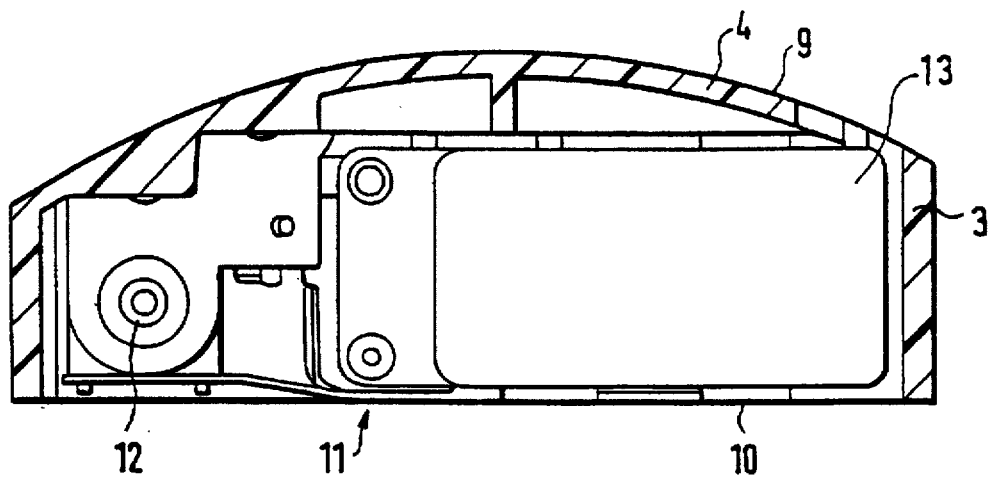
FIG. 2: A section through the blood pressure measuring module of FIG. 1 along the sectional face A—A.

The hermetic sealing of the casing 2 by mechanically stable support films 9 on the top of the casing cover 4 and support film 10 on the casing underside 11 can be gathered from FIG. 2. To the mechanically stable support films 9, 10 is applied a polyurethane-based hot-melt adhesive coating, so that the latter can be melted in the heat sealing process onto the casing 2. FIG. 2 also shows the one-piece construction of the casing frame 3 and the casing cover 4, as well as within the frame 3 pneumatic components such as the valve 12 and the pump 13.

Figure 3A:
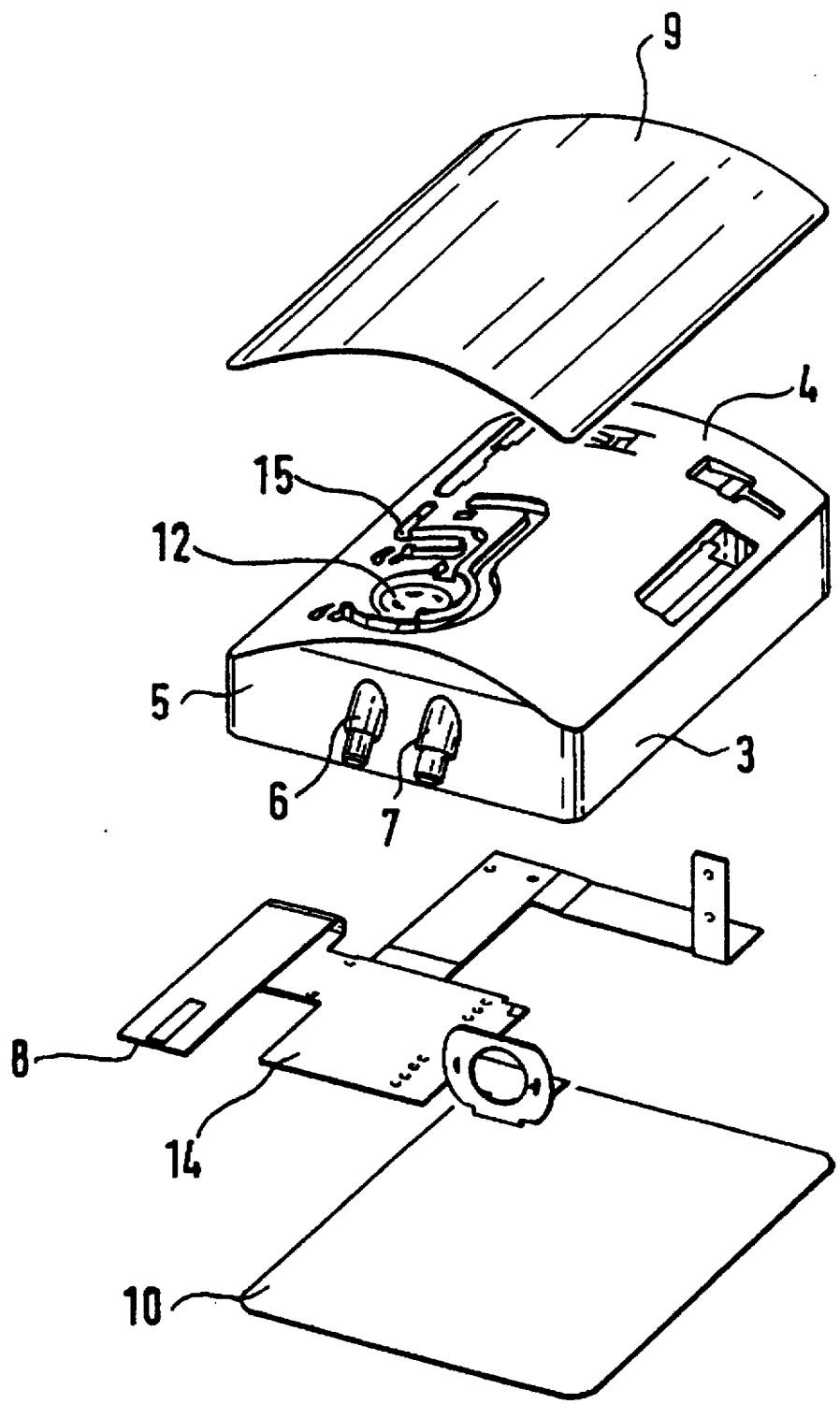
FIGS. 3a and 3b are a perspective exploded view of the blood pressure measuring module with the plastic casing, the two films and the flexible printed circuit board.
Figure 3B:
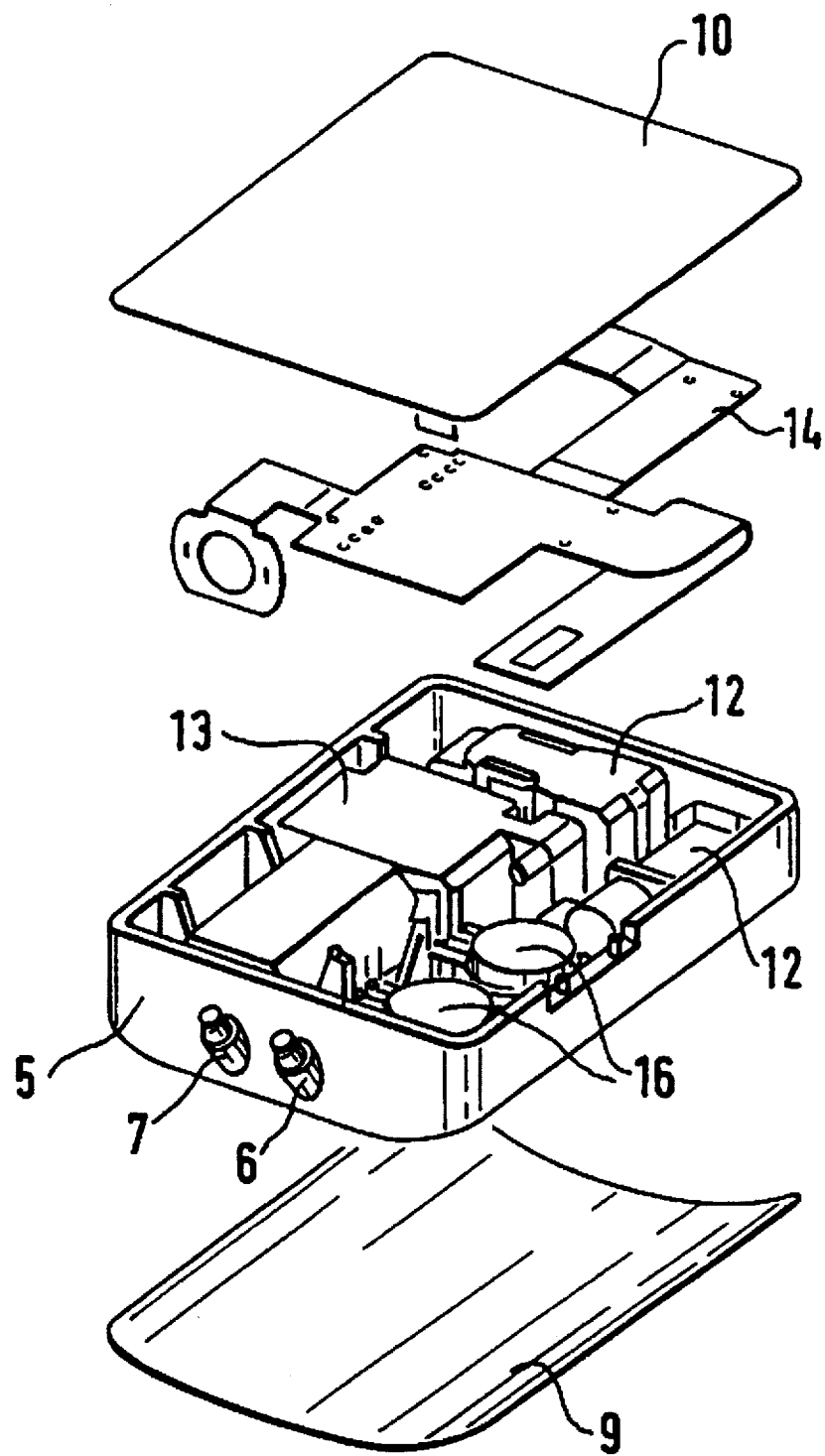

FIG. 3 shows in FIG. 3a the blood pressure measuring module 1 with the casing 2 in a view from above and in FIG. 3b in a view from below. FIG. 3 shows the support films 9, 10 and flexible printed circuit board 14 for the electrical connection of the electropneumatic components arranged within the casing frame 3 and separated from one another (exploded view).

FIG. 3a shows the pneumatic connecting lined in the form of ducts 15 arranged in the casing cover 4. It is also possible to see the opening for the check valve 12. The air passage 6 serves as an air outlet and the air passage 7 as an air inlet. The other openings in the cover are merely provided to facilitate manufacture by plastics injection moulding. For connecting the components use is made of a flexible circuit board 14 with external connecting lugs 8 for the power supply and signal transmission. Closure takes place by the application of mechanically stable support films 9, 10. FIG. 3b shows the individual components, such as the valve 12, pump 13 and pressure sensor 16, which are held on the casing frame 3 by means of conventional snap catches.

Figure 4A:
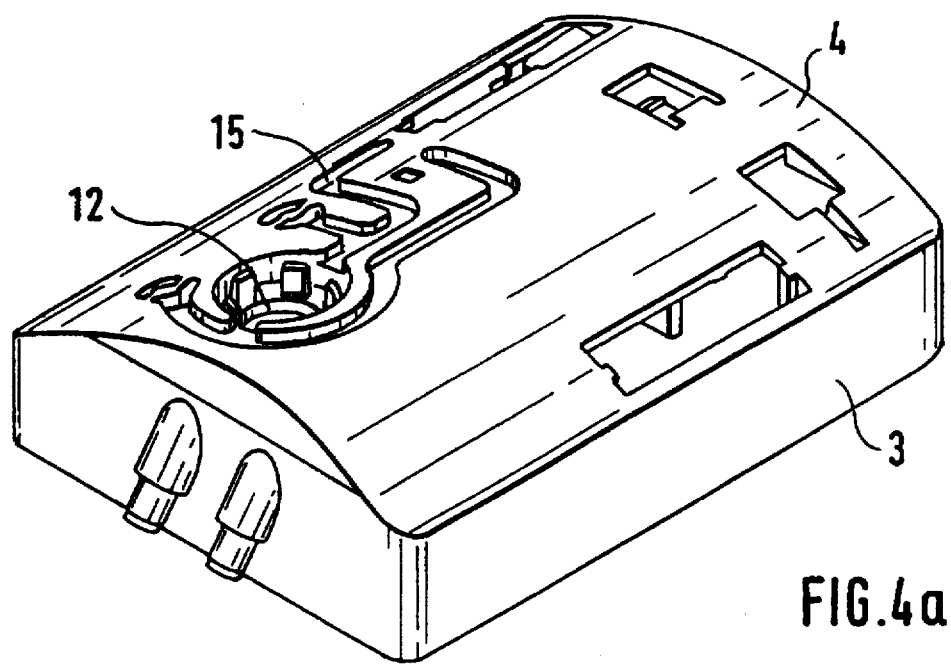
FIGS. 4a and 4b show a casing frame with the casing cover inside, without the individual components.
Figure 4B:
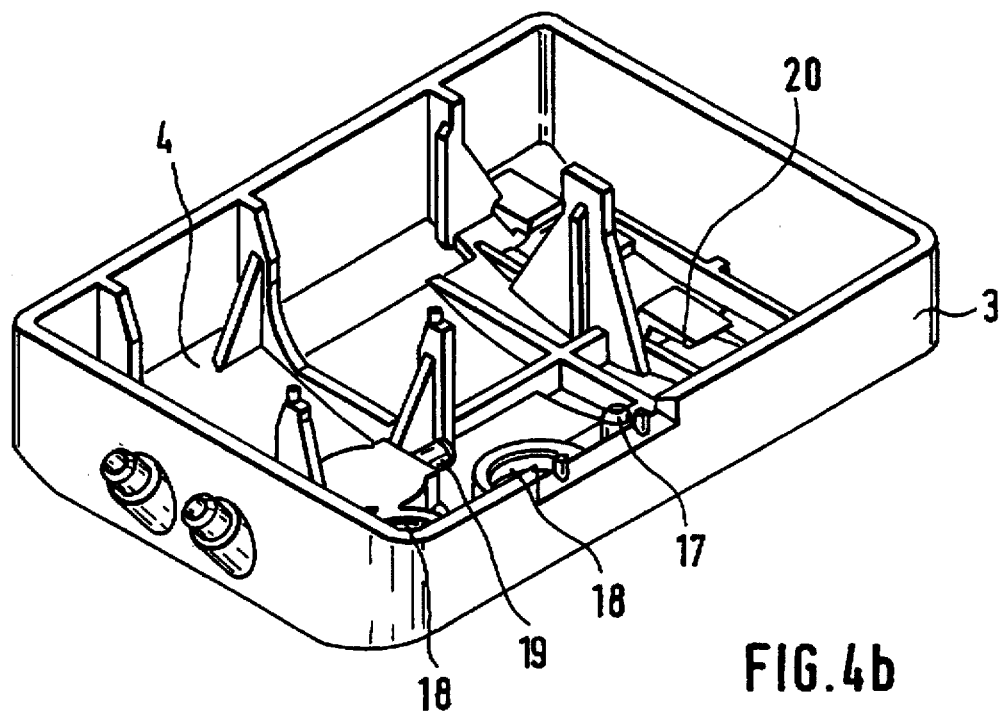

An enlarged view of the casing frame 3 and the casing cover 4 is depicted in FIG. 4a. FIG. 4b shows in a perspective view a casing frame 3 with casing cover 4 and without the components, so that it is possible to gather the internal design for the fixing of the individual components. In the casing cover there are individual openings permitting a connection between the components and the ducts 15. Thus, in FIG. 4b are shown the valve connection 17, sensor connections 18 and pump connection 19. By means of the snap-fit elements in the form of the snap catch 20 shown in exemplified manner, the individual components are held in position.

It is possible for redundancy reasons, as in the present embodiment, to duplicate certain components within the blood pressure measuring module, e.g. the pressure sensors 16. The individual components, such as pumps and microsensors are commercial components. The valve used can e.g. be that disclosed in DE 43 31 450 A1. As a result of the constructional measures according to the invention in conjunction with the corresponding components it is possible to implement an embodiment which is approximately 80 mm long, 60 mm wide and 22.5 mm high. This achieves a significant reduction in the size and integration of the elements. The inventive embodiment fulfills all the requirements with respect to the pressure accuracy and pumping time, which is below 6 seconds. The blood pressure measuring module in the pressure-side area is suitable for a permanent pressure of 39.9 kPa(300 mm Hg). The casing cover 4 and the corresponding support film 9 are together only 0.2 mm thick.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

I claim:

1. A blood pressure measuring module comprising:
   a hermetically sealed casing, which is sealed in a dust, water and pressure-tight manner by an exterior film on both a cover of said casing and an underside of said casing;
   a pump, positioned within said casing, for filling a blood pressure measuring cuff that is connectable to the module;
   a valve, positioned within said casing, for controllably venting of the cuff, pneumatic connecting lines, a pressure sensor, an electric control circuit and electric connecting lines for control of the valve, pump and pressure sensor; and
   wherein, said pneumatic connecting lines are integral with the casing cover, said casing cover being able to be pressurized while isolating a remainder of an inner area of said casing from pressurization.

2. A blood pressure measuring module according to claim 1, wherein the casing is constructed as a plastics injection moulding and includes a casing frame and a casing cover connected thereto.

3. A blood pressure measuring module according to claim 2, wherein the casing frame and casing cover are constructed in one piece.

4. A blood pressure measuring module according to claim 2, wherein the pneumatic connecting lines in the casing cover are constructed as ducts therein.

5. A blood pressure measuring module according to claim 2, wherein the valve, pump and pressure sensor are fixed to the casing frame.

6. A blood pressure measuring module according to claim 1, wherein the casing underside is formed by a mechanically stable support film.

7. A blood pressure measuring module according to claim 1, wherein the film includes a hot-melt adhesive coating.

8. A blood pressure measuring module according to claim 1, wherein the electrical control circuit comprises a flexible printed circuit board which extends from the casing for connection to a voltage source and control unit.

* * * * *